(12) United States Patent
Colleran et al.

(10) Patent No.: US 7,214,227 B2
(45) Date of Patent: May 8, 2007

(54) CLOSURE MEMBER FOR A MEDICAL IMPLANT DEVICE

(75) Inventors: Dennis Colleran, Frisco, TX (US); James Spitler, Frisco, TX (US)

(73) Assignee: Innovative Spinal Technologies, Mansfield, MA (US)

( * ) Notice: Subject to any disclaimer, the term of this patent is extended or adjusted under 35 U.S.C. 154(b) by 107 days.

(21) Appl. No.: 10/805,967

(22) Filed: Mar. 22, 2004

(65) Prior Publication Data
US 2005/0216000 A1     Sep. 29, 2005

(51) Int. Cl.
*A61B 17/58* (2006.01)
(52) U.S. Cl. ........................................... 606/61
(58) Field of Classification Search ................. 606/61, 606/72–73
See application file for complete search history.

(56) References Cited

U.S. PATENT DOCUMENTS

| | | | |
|---|---|---|---|
| 3,989,284 A * | 11/1976 | Blose | 285/332.2 |
| 4,041,939 A | 8/1977 | Hall | |
| 4,653,486 A | 3/1987 | Coker | |
| 4,917,409 A * | 4/1990 | Reeves | 285/334 |
| 4,950,269 A | 8/1990 | Gaines, Jr. | |
| 5,005,562 A | 4/1991 | Cotrel | |
| 5,034,011 A | 7/1991 | Howland | |
| 5,102,412 A | 4/1992 | Rogozinski | |
| 5,147,363 A | 9/1992 | Harle | |
| 5,261,913 A | 11/1993 | Marnay et al. | |
| 5,306,275 A | 4/1994 | Bryan | |
| 5,468,241 A | 11/1995 | Metz-Stavenhagen et al. | |
| 5,474,555 A | 12/1995 | Puno et al. | |
| 5,476,464 A | 12/1995 | Metz-Stavenhagen | |
| 5,507,745 A | 4/1996 | Logroscino et al. | |
| 5,562,663 A | 10/1996 | Wisnewski et al. | |
| 5,569,251 A | 10/1996 | Baker et al. | |
| 5,601,553 A | 2/1997 | Trebing et al. | |
| 5,605,457 A * | 2/1997 | Bailey et al. | 433/174 |

(Continued)

FOREIGN PATENT DOCUMENTS

| | | |
|---|---|---|
| DE | 299 03 342 | 6/1999 |
| DE | 298 10 798 | 10/1999 |
| EP | 1 190 678 | 3/2002 |
| EP | 1119304 | 12/2005 |
| WO | WO03/015648 A1 | 2/2003 |
| WO | WO/2004/041100 A1 | 5/2004 |
| WO | WO 2004/082464 | 9/2004 |

OTHER PUBLICATIONS

International Search Report and Written Opinion issued for PCT/US2005/009616 dated Oct. 4, 2005.

*Primary Examiner*—Eduardo C. Robert
*Assistant Examiner*—Annette Reimers
(74) *Attorney, Agent, or Firm*—Carr LLP

(57) ABSTRACT

A closure member, such as a set screw, and complementary receiving member are included in a medical implant device. The receiving member has a plurality of noncontiguous, threaded walls substantially defining a bore for receiving the threaded closure member. When the closure member is inserted into the receiving member, their respective threads interlock to join the noncontiguous walls of the receiving member. The closure member has an outer thread configured to interlock with the inner walls of the receiving member in a manner that aids in preventing the noncontiguous walls of the receiving member from moving away from the closure member. In certain embodiments, the closure member's outer thread includes a trailing edge having a point that is rearward of the trailing edge's root, and the outer thread includes a leading edge having a point that is forward of the leading edge's root.

31 Claims, 6 Drawing Sheets

U.S. PATENT DOCUMENTS

| | | | |
|---|---|---|---|
| 5,605,458 A * | 2/1997 | Bailey et al. | 433/174 |
| 5,607,304 A * | 3/1997 | Bailey et al. | 433/174 |
| 5,607,425 A | 3/1997 | Rogozinski | |
| 5,607,428 A | 3/1997 | Lin | |
| 5,611,800 A | 3/1997 | Davis et al. | |
| 5,628,740 A | 5/1997 | Mullane | |
| 5,662,653 A | 9/1997 | Songer et al. | |
| 5,669,911 A | 9/1997 | Errico | |
| 5,672,176 A | 9/1997 | Biedermann et al. | |
| 5,683,390 A | 11/1997 | Metz-Stavenhagen et al. | |
| 5,697,929 A | 12/1997 | Mellinger | |
| 5,716,355 A | 2/1998 | Jackson | |
| 5,723,013 A | 3/1998 | Jeanson et al. | |
| 5,725,527 A | 3/1998 | Biedermann et al. | |
| 5,728,098 A | 3/1998 | Sherman et al. | |
| 5,733,286 A | 3/1998 | Errico et al. | |
| 5,752,957 A | 5/1998 | Ralph et al. | |
| 5,782,833 A | 7/1998 | Haider | |
| 5,879,350 A | 3/1999 | Sherman | |
| 6,074,391 A * | 6/2000 | Metz-Stavenhagen et al. | 606/61 |
| 6,254,146 B1 * | 7/2001 | Church | 285/334 |
| 6,296,642 B1 * | 10/2001 | Morrison et al. | 606/61 |
| 6,302,888 B1 * | 10/2001 | Mellinger et al. | 606/73 |
| 6,454,768 B1 | 9/2002 | Jackson | |
| 6,530,929 B1 | 3/2003 | Justis et al. | |
| 6,582,434 B2 | 6/2003 | Kawakami | |
| 6,726,689 B2 * | 4/2004 | Jackson | 606/73 |
| 6,835,196 B2 | 12/2004 | Bierdermann | |
| 6,840,941 B2 | 1/2005 | Rogers | |
| 6,843,791 B2 | 1/2005 | Serhan | |
| 6,887,242 B2 | 5/2005 | Doubler | |
| 6,893,443 B2 | 5/2005 | Fregg | |
| 6,905,500 B2 | 6/2005 | Jeon | |
| 6,911,030 B1 | 6/2005 | Vanacker | |
| 6,932,817 B2 | 8/2005 | Baynham | |
| 2004/0039384 A1 | 2/2004 | Boehm, Jr. et al. | |
| 2004/0049196 A1 * | 3/2004 | Jackson | 606/73 |
| 2004/0138662 A1 | 7/2004 | Landry | |
| 2004/0236330 A1 | 11/2004 | Purcell | |
| 2004/0254574 A1 | 12/2004 | Morrison | |
| 2004/0260283 A1 | 12/2004 | Wu | |
| 2004/0260284 A1 | 12/2004 | Parker | |
| 2004/0260285 A1 | 12/2004 | Steib | |
| 2004/0260287 A1 | 12/2004 | Ferree | |
| 2005/0033436 A1 | 2/2005 | Sehlapfer | |
| 2005/0070899 A1 | 3/2005 | Doubler | |
| 2005/0070901 A1 | 3/2005 | David | |
| 2005/0080415 A1 | 4/2005 | Keyer | |
| 2005/0080419 A1 | 4/2005 | Donath | |
| 2005/0080420 A1 | 4/2005 | Farris | |
| 2005/0090833 A1 | 4/2005 | DiPoto | |
| 2005/0096653 A1 | 5/2005 | Doubler | |
| 2005/0096654 A1 | 5/2005 | Lin | |
| 2005/0113833 A1 | 5/2005 | Davison | |
| 2005/0119658 A1 | 6/2005 | Ralph | |
| 2005/0131404 A1 | 6/2005 | Maxda | |
| 2005/0131410 A1 | 6/2005 | Lin | |
| 2005/0131545 A1 | 6/2005 | Chervitz | |
| 2005/0137594 A1 | 6/2005 | Doubler | |
| 2005/0149023 A1 | 7/2005 | Ritland | |
| 2005/0154391 A1 | 7/2005 | Doherty | |
| 2005/0154393 A1 | 7/2005 | Doherty | |
| 2005/0159750 A1 | 7/2005 | Doherty | |
| 2005/0165400 A1 | 7/2005 | Fernandez | |
| 2005/0171537 A1 | 8/2005 | Mazel | |
| 2005/0171538 A1 | 8/2005 | Sgier | |
| 2005/0175142 A1 | 8/2005 | Biedermann | |
| 2005/0177154 A1 | 8/2005 | Moumene | |

* cited by examiner

CLOSURE MEMBER FOR A MEDICAL IMPLANT DEVICE

TECHNICAL FIELD

The present invention relates generally to the field of medical implant devices, and more particularly to medical implant devices which utilize a closure means for joining two components. More specifically, the invention relates to an apparatus which is particularly useful in closing a medical implant device and preventing splaying of parts of the medical implant device. Embodiments of the present invention provide a closure member, such as a set screw, that includes an external thread that is configured to aid in preventing noncontiguous walls of the structure within which the closure member is placed from moving away from the closure member.

BACKGROUND OF THE INVENTION

Set screws are used in many ways in order to lock one element of a device relative to another. Set screws are quite important in the art of medical implants, as it is often necessary to capture one element of the implant relative to another and to then lock the two relative to one another to prevent subsequent movement therebetween. Failure to properly lock two elements of a medical implant together may result in failure of the implant and possible serious injury to the patient within which the implant is placed.

For instance, orthopedic injuries, deformities, and degenerative diseases often require intervention in the form of surgery for placing implants to stabilize an internal structure, promote healing, and relieve pain. In the area of spinal surgery, for example, a common procedure includes placement of bone securing elements in the form of screws or hooks that are joined by a connecting rod spanning between these elements. Once placed, the rod must be firmly secured to the bone securing elements to provide a stable construct which effectively immobilizes a corresponding portion of the spine. For this, large forces are applied to the construct typically in the form of a set screw or locking element which presses firmly against the rod to secure the rod to the bone securing element (e.g., pedicle screw or other anchor element).

Additionally, it is generally desirable for these spinal implants to maintain a small profile so as to minimize the impact upon the patient. The loading required to lock the components can cause component deformation in these low profile implants, resulting in assembly loosening and possible implant failure. Specifically, when spinal loading occurs postoperatively, the walls of the securing element trapping the rods may be forced outward causing the rod to be released and allowing room for play in the rod.

As an example configuration of a vertebral stabilization implant device, anchors (e.g., pedicle screws) are connected to the vertebrae and are connected to one another by a connecting means, such as a brace or rod. For instance, a first pedicle screw may be coupled to a first vertebral level and a second pedicle screw may be coupled to another vertebral level, and a distraction rod is used to connect the first and second pedicle screws. The head of the pedicle screw (or a receiving member coupled thereto) is typically fork-shaped. With annular pedicle screw heads a distraction rod is guided through and is fixed on both sides of the head with the help of a nut. With fork-shaped heads, inner (female) threaded sections are included within the heads for receiving a set screw for applying direct or indirect pressure on a previously inserted distraction rod for securing such distraction rod relative to the pedicle screws. A similar receiving part for a distraction rod or likewise is also known for hook-like retaining components, for example with so-called lamina hooks or pedicle hooks which are hooked into the corresponding vertebrae parts.

Conventional set screws for use in medical implant devices typically utilize threads which are referred to as unified threads, which have a V-shaped cross-section. That is, the edges of the unified thread's cross-section form a V shape. V-shaped threads work reasonably well in devices where a bore is provided that completely surrounds the set screw and has a mating thread that mates with the thread of the set screw. However, many medical implants, such as open-headed (or "open-back") bone screws have a receiving member (or "rod cage") coupled to the pedicle screw head, which does not provide for a bore that will entirely encircle the set screw. For example, the above-mentioned fork-shaped receiving member typically has a channel formed by a plurality of noncontiguous (or discontinuous) walls that include an inner (female) thread that forms a helical spiral about a center longitudinal axis of the channel. That is, the walls forming the channel have a noncontiguous diameter. Such receiving member, in certain implementations, effectively provide a cylindrical sleeve that has a longitudinal slit in one or more planes for at least part of its length.

In such implementations, the set screw is inserted into the channel (or sleeve) of such fork-shaped receiving member. Accordingly, in this type of implant device, the set screw also functions as a closure member and spans between a pair of discontinuous threaded surfaces. When V-shape threaded set screws are utilized for this purpose, the forces exerted by the set screw during torquing are partially parallel to the axis of rotation of the set screw and partially radially extending outwardly from the set screw. The radial outward forces can and frequently do spread the arms (or noncontiguous "walls") of the receiving member within which the set screw is being torqued sufficiently to allow for failure of the set screw. Other example types of set screws proposed for use with such noncontiguous wall implementations (or "open-back configurations") for functioning as a closure member that spans between a pair of noncontiguous threaded surfaces within a medical implant device are described in U.S. Pat. No. 6,454,768 to Jackson, U.S. Pat. No. 6,074,391 to Metz-Stavenhagen et al., and U.S. Pat. No. 6,296,642 to Morrison et al.

A further difficulty that has been experienced with such noncontiguous wall implementations as the above fork-shaped receiving member configurations is that the upright legs or wall sections of the set screw receiving member can experience splaying after implantation. For example, in the spinal field, after a rod is placed into the channel in the body portion of an open-back spinal fixation element, a closure or locking element is typically engaged in the body portion over the rod to clamp it within the channel so that there is no relative movement between the rod and the fixation element. Since no relative motion is possible, stresses placed on the rod after implantation are transmitted via the fixation element to the bone. In some cases, these stresses cause the legs or wall sections of the fixation element (such as the fork-shaped receiving member mentioned above) on either side of the slot to splay or move away from each other. Significant splaying of the fixation element generally results in its failure, since the closure or locking element will loosen its clamping of the rod. When that happens, the rod is free to move with respect to the fixation element, and may become disconnected with the fixation element altogether. In such a case, the therapeutic value of the implant is obviated, and further injury or complications may also result.

To prevent splaying of the noncontiguous walls, prior medical implant devices have included a nut, cap, clamp or similar apparatus to surround and hold the walls of the fixation element together. For example, in U.S. Pat. No. 5,672,176 to Biedermann et al., a rod is placed into a slot in the fixation element, the locking member is engaged with the fixation element to press down via an intermediary part on the rod, and an outer nut is threaded on the outside of the fixation element. Although effective in controlling splaying, these devices have tended to be relatively more expensive and less efficient to implant compared with devices without an outer nut or cap. The outer nut or cap also adds to the profile of the medical implant device, making the device more difficult to implant in the frequently limited area in which to perform surgery and/or place an implant. A larger implant can also result in a higher risk of residual pain to the patient or potential complications.

There is therefore a need remaining in the industry for medical implant devices, and particularly orthopedic devices, which minimize the profile and bulk of the components of the device and minimizes the cost and difficulty of using such devices, while still preventing splaying of the noncontiguous walls of fixation elements. For instance, it is desirable to have a closure member, such as a set screw, that is configured to aid in preventing (rather than urging) the opposing walls of an implant from pulling away from the closure member.

BRIEF SUMMARY OF THE INVENTION

Embodiments of the present invention provide a closure member, such as a set screw, and complementary receiving member for use in a medical implant device. The receiving member has a plurality of noncontiguous walls substantially defining a bore for receiving the closure member. The receiving member further comprises inner (female) threads cut into the inner sides of the walls, which are complementary to outer (male) threads of the closure member. Thus, when the closure member is inserted into the receiving member, their respective threads interlock to join the noncontiguous walls of the receiving member. In accordance with various embodiments provided herein, the closure member has an outer thread that is configured to interlock with the inner walls of the receiving member in a manner that aids in preventing the noncontiguous walls of the receiving member from moving away from the closure member. Thus, embodiments provided herein aid in preventing splaying of the noncontiguous receiving member.

Various outer thread configurations of the closure member (and complementary inner thread configurations of the receiving member) are provided herein. According to various embodiments of the present invention, the outer thread of the closure member is a helical spiral about a cylindrical body (the helical spiral having a pitch), and the outer thread includes a trailing edge having a point that is rearward of the trailing edge's root (adjacent the cylindrical body) relative to the direction of advancement of the closure member when being inserted into the receiving member. Further, the outer thread includes a leading edge having a point that is forward of the leading edge's root relative to the direction of advancement of the closure member when being inserted into the receiving member. Thus, the trailing edge's point that is rearward of its root and the leading edge's point that is forward of its root, when interlocked with complementary inner threads of the receiving member, aids in preventing the receiving member's noncontiguous walls from separating from the closure member.

When formed in a helical pattern, the thread configuration of certain embodiments provided herein (such as the example dovetail configuration described further below) completely disallows a problem know as cross threading wherein the first leading edge of a thread or helical geometry can start in a position other than the first turn. This is due to the nature of the geometry in which the thread has a thickness at some point crestward of its root that is greater than the root's thickness. Therefore, because of this configuration the outer thread of the closure member will not engage the incorrect turn of the receiving member's inner thread and start to cross thread. This prevents the user from considering the assembly fully tightened, when in realty it is not. If such cross threading were allowed to happen, instability, implant failure and implant removal would potentially result.

Additionally, the interlocking threaded configurations of certain embodiments provided herein induces a radial inward force that aids in rod securement of a bone fixation device. For instance, in certain embodiments, the receiving member is a head of a bone fixation device, such as a pedicle screw. As is common in various spinal stabilization procedures, a first such bone fixation device may be coupled to a first vertebrae and a second such bone fixation device may be coupled to a second vertebrae, and a rod (or brace) may be used to couple the two bone fixation devices. For instance, one end of the rod may be inserted into the receiving member of the first bone fixation device (e.g., via a channel that is transverse to the longitudinal bore defined by the receiving member's noncontiguous walls), and the opposing end of the rod may be inserted into the receiving member of the second bone fixation device (e.g., via a channel that is transverse to the longitudinal bore defined by that receiving member's noncontiguous walls). A closure member, such as a set screw, may then be coupled within each of the receiving members to interlock the respective noncontiguous walls of the receiving members and to apply, either directly or indirectly, force against the end of the rod included in the respective receiving member so as to secure such end to its respective bone fixation device. The thread geometry of certain embodiments of the closure and receiving members provided herein effectively draws the interior walls of the receiving member that support the rod inward toward the rod as the closure member interlocks with the receiving member's walls. This amplifies the clamping force subjected to the rod in this type of medical implant device. This feature further aids in overall construct stability and the ability to withstand cyclical loading without failure.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION

Figure 1:
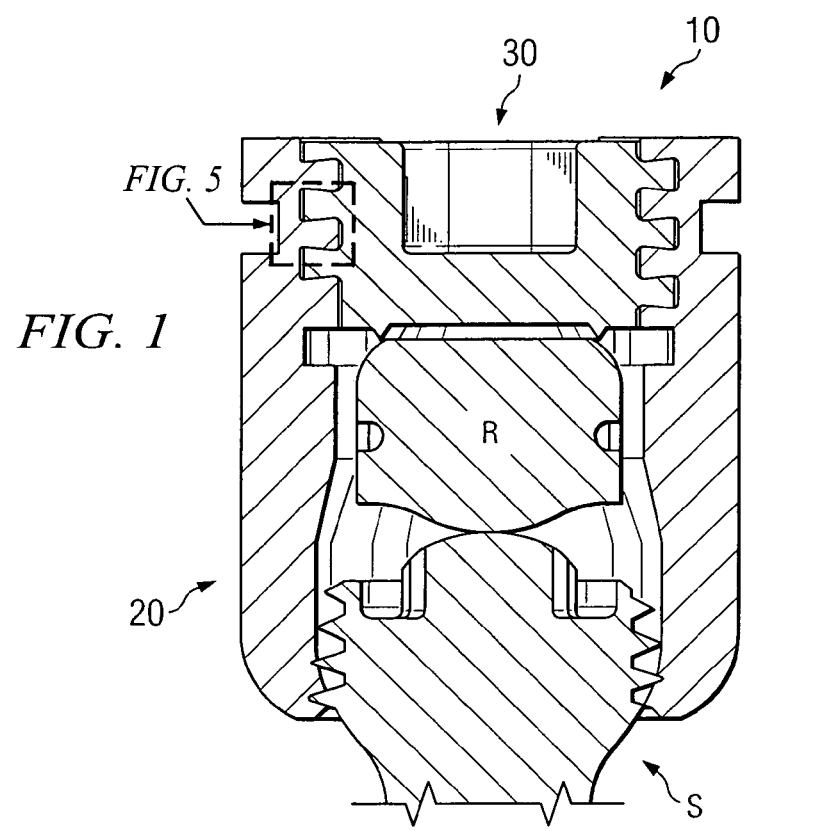
FIG. 1 shows a cross-section view of an example medical implant device 10 that includes a closure member 30 interlocked with a noncontiguous receiving member 20 in accordance with one embodiment of the present invention.

Various embodiments of the present invention are now described with reference to the above figures. As described further below, various embodiments are disclosed for a closure member and complementary receiving member that is particularly useful in medical implant devices. More particularly, in accordance with certain embodiments, a noncontiguous receiving member is included in a medical implant device. The noncontiguous receiving member includes a channel formed by a plurality of noncontiguous walls that include an inner (female) thread that forms a helical spiral about a center longitudinal axis of the channel. That is, the walls forming the channel have a noncontiguous diameter. Such receiving member, in certain implementations, is a cylindrical sleeve that has a longitudinal slit in one or more planes for at least part of its length. A closure member (e.g., set screw) has an outer (male) thread that is configured as a helical spiral about a center longitudinal axis of the closure member. The closure member is received into the channel and its outer (male) thread engagingly interlocks with the inner (female) thread of the receiving member. Thus, the closure member spans the noncontiguous threads of the receiving member's walls to close such receiving member. Various embodiments of the outer (male) thread of the closure member and complementary inner (female) thread of the receiving member are provided, which aid in preventing splaying of the receiving member.

In accordance with certain embodiments, the closure member comprises a body (e.g., an elongated cylindrical body) about which an outer (male) thread is spiraled. Preferably, the body portion and outer thread portion are integral. The outer thread has a root that is adjacent the closure member's body. The outer thread has a crest that is a point furthest from a center longitudinal axis of the closure member's body (when measured along a line that is perpendicular to the center longitudinal axis of the closure member's body). Generally, a thread's crest is that surface of the thread which joins the flanks of the thread and is farthest from the cylinder (body) from which the thread projects. The outer thread has a trailing-edge surface (or "load flank") that faces away from the direction of advancement of the closure member when such closure member is being inserted into a receiving member. The outer thread also has a leading-edge surface (or "forward flank") that faces toward the direction of advancement of the closure member when such closure member is being inserted into a receiving member. In some instances, a plurality of edges that each face rearward (away from the direction of advancement of the closure member) may form the trailing-edge surface, and a plurality of edges that each face forward (toward the direction of advancement of the closure member) may form the leading-edge surface. For instance, the full length of each of the trailing and leading edges (from root to crest) may not have consistent slopes. Further, the trailing-edge surface (or portions thereof) need not be perpendicular to the longitudinal axis of the closure member to face perfectly rearwardly, but may instead face generally rearwardly. In other words, when breaking the angle(s) of the trailing-edge surface into their component parts, there will exist some rearward facing component. Similarly, the leading-edge surface (or portions thereof) need not be perpendicular to the longitudinal axis of the closure member to face perfectly forwardly, but may instead face generally forwardly. In other words, when breaking the angle(s) of the leading-edge surface into their component parts, there will exist some forward facing component.

As further described herein, each of the trailing and leading edges have a root and a crest. The root of each surface is where such surface is adjacent to the closure member's body. The crest of the trailing-edge surface is a point on that surface that is furthest from a center longitudinal axis of the closure member's body (when measured along a line that is perpendicular to the center longitudinal axis of the closure member's body), and the crest of the leading-edge surface is a point on that surface that is furthest from a center longitudinal axis of the closure member's body (when measured along a line that is perpendicular to the center longitudinal axis of the closure member's body). In certain implementations, the crest of the trailing and leading edge surfaces may be a common point. In certain embodiments, the crest of the thread is a longitudinal surface that connects the trailing edge and the leading edge (e.g., connects the crest of the trailing edge and the crest of the leading edge), wherein all points along such longitudinal surface are equally distant from the center longitudinal axis of the closure member's body (when measured along a line that is perpendicular to the center longitudinal axis of the closure member's body).

In accordance with at least one embodiment, the outer thread of the closure member comprises substantially a dovetail shape (in cross-section). In certain embodiments, the trailing-edge surface of the thread slopes rearwardly from the thread's root toward the thread's crest, while the leading-edge surface of the thread slopes forwardly from the thread's root toward the thread's crest. Thus, in certain implementations, the trailing-edge surface of the thread has a slope from root to crest that is opposite the slope of the leading-edge surface of the thread from root to crest. In certain implementations, the thread's crest is thicker than its root.

In certain embodiments, the closure member's thread includes at least one point between its root and crest that is thicker than the thread's root. In certain embodiments, the thread includes at least one point between its root and crest that is thicker than both the thread's root and the thread's crest.

In certain embodiments, the trailing-edge surface of the closure member's thread includes at least one point between its root and its crest that is rearward of its root relative to the direction of advancement of the closure member, and the leading-edge surface includes at least one point between its root and its crest that is forward of its root relative to the direction of advancement of the closure member. In certain embodiments, the trailing-edge surface of the closure member's thread includes at least one point between its root and its crest that is rearward of both its root and its crest relative to the direction of advancement of the closure member, and the leading-edge surface includes at least one point between its root and its crest that is forward of both its root and crest relative to the direction of advancement of the closure member.

In accordance with certain embodiments, the trailing-edge surface of the closure member's thread includes a first slope between a first point and a second point on the trailing-edge surface relative to a longitudinal axis of the closure member, wherein the second point is nearer the crest than the first point, and the leading-edge surface includes a second slope between a first point and a second point on the leading-edge surface relative to the longitudinal axis of the closure member, wherein the second point is nearer the crest than the first point and wherein the second slope is in an opposite direction than the first slope.

In accordance with certain embodiments, at least one of the trailing-edge and leading-edge surfaces of the closure member's thread have a non-uniform slope from root to crest. That is, at least one of the trailing-edge and leading-edge surfaces of the closure member's thread have a first slope relative to a longitudinal axis of the closure member between a first point and second point along such surface, and a second slope relative to a longitudinal axis of the closure member between the second point and a third point along such surface, wherein the first and second slopes are different. In certain embodiments, both the trailing-edge surface and leading-edge surface have such non-uniform slope from root to crest. As one example, in one embodiment, the trailing-edge surface slopes rearwardly from a first point adjacent the root to a second point and then slopes forwardly from the second point to a third point adjacent the crest. In certain implementations of this example embodiment, the crest is arranged substantially horizontal with the root (i.e., a lateral axis from the crest to the root is substantially perpendicular with the closure member's longitudinal axis), and a point between the root and crest (e.g., the "second point" in this example) on the trailing-edge is rearward of the root.

Examples of various such embodiments, which aid in preventing splaying of the receiving member, are described further below in connection with FIGS. 1–10.

FIG. 1 shows a cross-section view of an example medical implant device 10 that may be used to immobilize a spinal segment in accordance with one embodiment of the present invention. Medical implant device 10 comprises a receiving member 20. In this example, receiving member 20 is a noncontiguous member. That is, as described further with FIG. 2 below, receiving member 20 includes a longitudinal channel formed by a plurality of noncontiguous walls that include an inner (female) thread that forms a helical spiral about a center longitudinal axis of the channel.

Medical implant device 10 further comprises a closure member (e.g., a set screw) 30, which is adapted to interlock with receiving member 20. That is, closure member 30 includes an outer (male) thread configured to interlock with the inner (female) thread of the noncontiguous walls of receiving member 20 in order to close such receiving member 20 (i.e., interlock the noncontiguous walls of receiving member 20). Medical implant device 10, in the illustrated embodiment, is a bone fixation device used to connect an elongated member R, which may be referred to as a "rod" or "brace," to a bone by way of a bone fixation member S, such as a pedicle screw or other "anchor element." Of course, embodiments of the present invention are not limited in application solely to such a bone fixation device, but may equally be utilized within various other types of medical implant devices for closing noncontiguous walls of a receiving member included in such medical implant devices.

Figure 2:
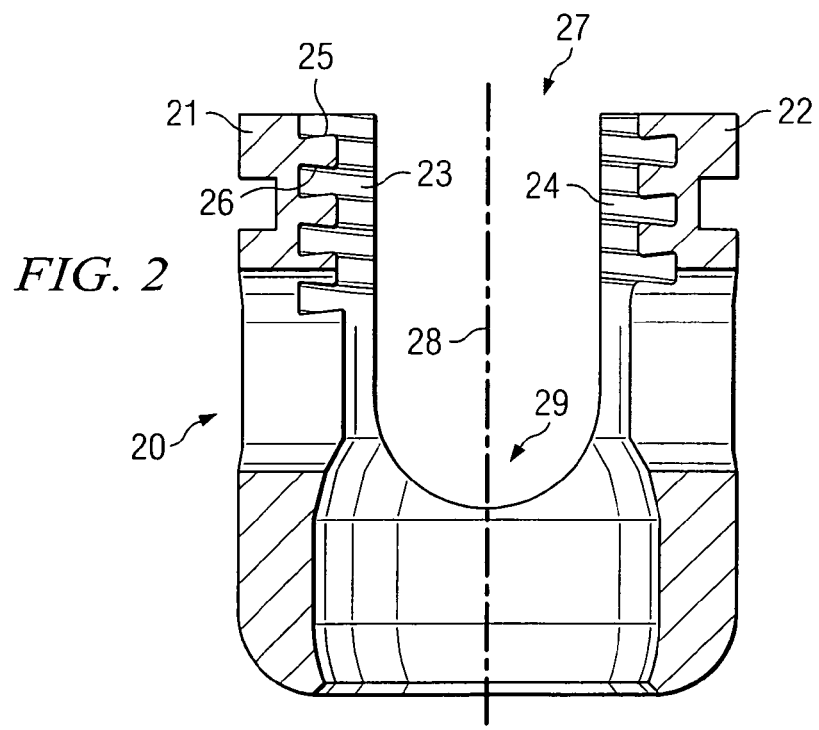
FIG. 2 shows a cross-section view of receiving member 20 of FIG. 1.

FIG. 2 shows a cross-section of the receiving member 20 having a central, longitudinal bore 27 in which closure member 30 is received. Longitudinal bore 27 of receiving member 20 is formed within noncontiguous walls 21 and 22 and is centered on axis 28. Receiving member 20 also includes a transverse channel 29, which is substantially normal (or "perpendicular") to longitudinal bore 27, for receiving elongated member R. Channel 29 is formed by outer walls 21 and 22. Receiving member 20 also includes interlocking features (e.g., "inner" or "female" thread) 23 and 24 cut into side walls 21 and 22, respectively. Interlocking features 23 and 24 are centered about axis 28 in the form of a helical pattern having rearward-facing surface 25 (which faces the opening of bore 27, i.e., faces the direction opposite the direction of advancement of closure member 30 when it is being inserted into receiving member 20) and forward-facing surface 26 (which faces toward channel 29 or elongated element R (FIG. 1), i.e., faces the direction of advancement of closure member 30 when it is being inserted into receiving member 20). Surfaces 25 and 26 are cut in such a manner to form a complementary interlocking geometry relative to the geometry of interlocking feature (e.g., "outer" or "male" thread) of the closure member. In this example, surfaces 25 and 26 are cut in such a manner to form an interlocking dovetail geometry that is complementary to the dovetail geometry of interlocking feature 33 of closure member 30 described further below in connection with FIG. 3.

Figure 3:
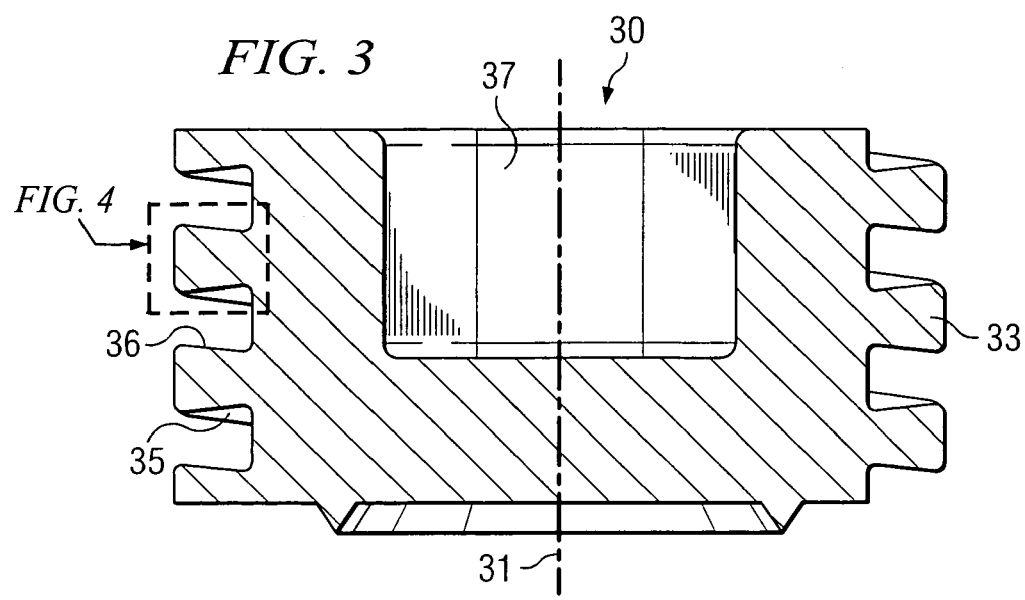
FIG. 3 shows a cross-section view of closure member 30 of FIG. 1.

FIG. 3 shows a cross-section of closure member 30, in accordance with one embodiment, centered on longitudinal axis 31. When being inserted in receiving member 20, axis 31 of closure member 30 is coaxial with longitudinal axis 28 of bore 27. Closure member (e.g., set screw) 30 includes external interlocking features (e.g., "outer" or "male" thread) 33 centered about axis 31 in the form of a helical pattern. In this example, interlocking features 33 include leading-edge surface 35 and trailing-edge surface 36 configured to form a dovetail pattern suitable for mating to surfaces 25 and 26 of interlocking features 23 and 24 of receiving member 20 as described further herein. Closure member 30 also includes a recess area 37 adapted with suitable drive features for the purpose of transferring torque to turn interlocking features 33 into interlocking dovetail features 23 and 24 of receiving member 20 for the purpose of forcibly compressing elongated member R and bone fixation member S between receiving member 20 and closure member 30.

Figure 4:
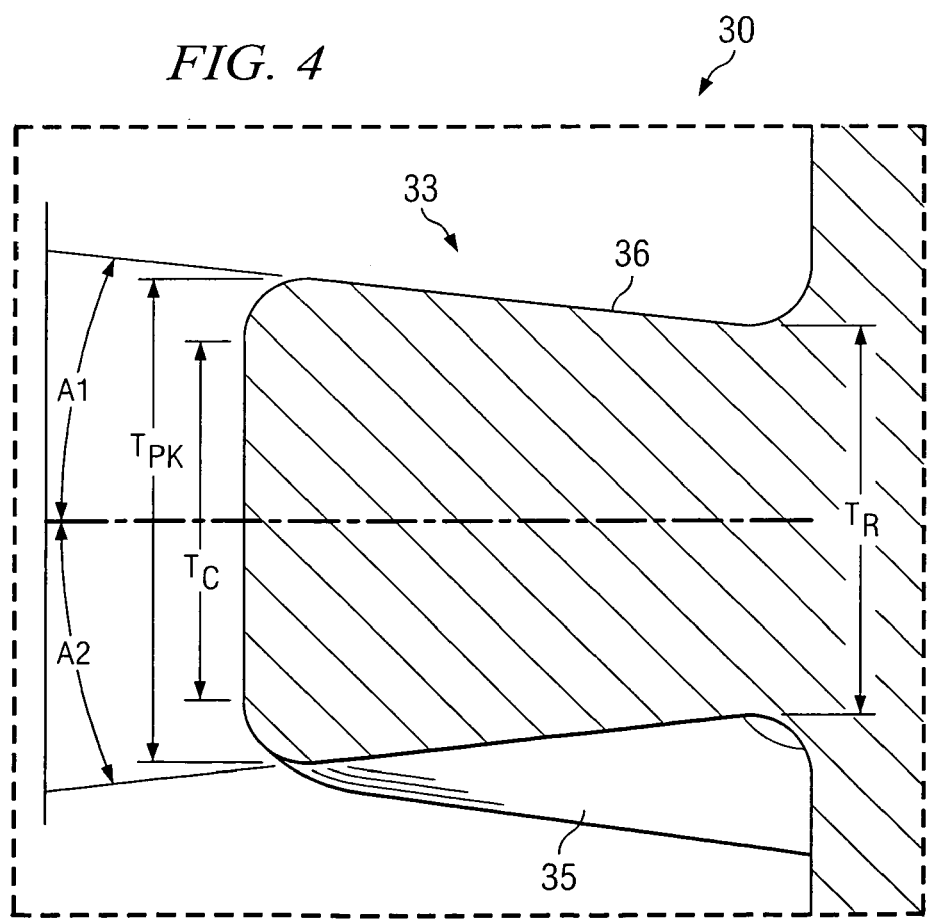
FIG. 4 shows a cross-section view of a example thread of closure member 30 according to one embodiment of the present invention.

Turning to FIG. 4, a cross-section detailed view of interlocking dovetail feature (also referred to herein as a "thread") 33 of closure member 30 according to one embodiment is shown. In this example, outer thread 33 includes leading edge 35, which, during the insertion or closure process, is introduced into central bore 27 of receiving member 20 (shown in FIG. 2) first wherein it engages rearward-facing surface 25 of mating female interlocking dovetail feature 23 (which may also referred to herein as "inner thread" or "female thread"). As closure member 30 rotatably advances along longitudinal axis 28 within bore 27, trailing edge 36 of thread 33 then engages forward-facing surface 26 of female thread 23.

Angles A1 and A2 of FIG. 4 establish an offset height difference between the relative heights (or "thicknesses") of the root and a point crestward along the closure member's thread 33. In this example, the thickness $T_R$ at the root of thread 33 is smaller than the peak thickness $T_{PK}$ at a point crestward along thread 33. In this example, the thickness $T_C$ of thread 33 at its crest (or point furthest from central axis 31 when measuring a straight line that is perpendicular to central axis 31 from such point to the central axis 31) is equal to or larger than the thickness $T_R$ at the thread's root. The thread's crest in this example is a longitudinal surface that connects the trailing edge 36 and the leading edge 35, wherein all points along such longitudinal surface are equally distant from central axis 31 (when measuring a perpendicular line from such point to the central axis 31). As shown in this example, the thread's maximum (or peak) thickness $T_{PK}$ occurs at a point closer to the thread's crest than its root. In certain implementations, thread 33 may be configured such that its thickest point $T_{PK}$ occurs at the crest. As closure member 30 is turned down through central bore 27 of receiving member 20, the mating interlocking dovetail features 33 of closure member 30 interact with dovetail features 23 and 24 of walls 21 and 22 to mechanically secure one within the other.

Figure 5:
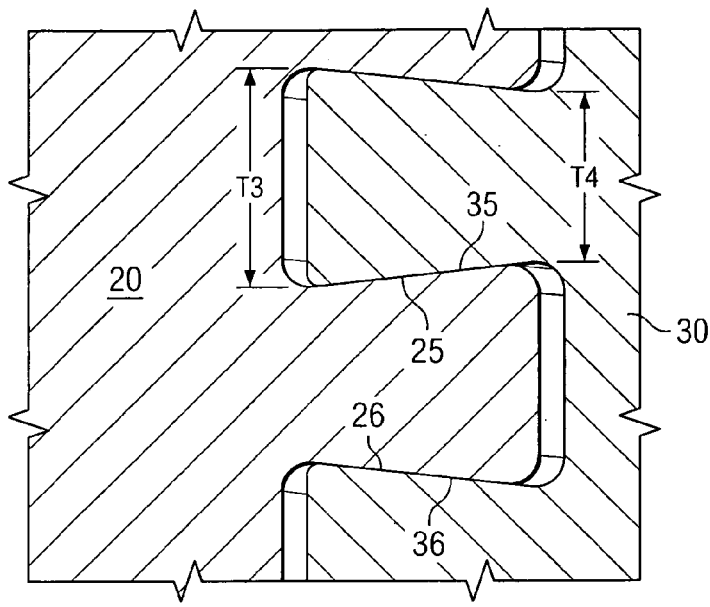
FIG. 5 shows a cross-section view of the example thread of closure member 30 of FIG. 4 interlocking with complementary (or female) thread of receiving member 20 of FIG. 2.

FIG. 5 shows a cross-section of receiving member 20 of FIG. 2 and closure member 30 of FIG. 3 when joined together. As can be seen, forward-facing surface 26 of receiving member 20 engages with trailing-edge surface 36 of thread 33 of closure member 30, while rearward-facing surface 25 of receiving member 20 engages with leading-edge surface 35 of thread 33 of closure member 30. Because peak thickness T3, which is greater than root thickness T4, occurs crestward along the female thread 23 of receiving member 20 (wherein the female thread's crest is the point furthest from central axis 28 of bore 27 when measuring a straight line that is perpendicular to central axis 28 from such point to the central axis 28), a mechanical interlock in the form of a dovetail is created between the female (or inner) thread 23 of receiving member 20 and the male (or outer) thread 33 of closure member 30 such that surfaces 25 and 26 of female thread 23 cannot be separated from surfaces 35 and 36 of thread 33. In this way, closure member 30 forbids walls 21 and 22 from separating or splaying relative to such closure member 30. This action prevents the elongated member R from obtaining room to rock within transverse channel 29 which is beneficial because, as mentioned above, if elongated member R obtained room to rock it could cause device failure and required replacement and/or injury to the patient. Additionally, when tightened, surfaces 35 and 36 act to direct radial forces inward toward central axis 28 thereby further compressing elongated member R between side walls 21 and 22. Thus, the example closure member 30 applies forces to compress noncontiguous walls 21 and 22 of receiving part 20 together, while also applying forces, either directly or indirectly, to elongated member R to secure its position relative to anchor (e.g., pedicle screw) S.

In accordance with certain embodiments, the peak thickness of the thread is not uniform along the entire helical spiral. For instance, in certain embodiments, the peak thickness $T_{PK}$ is greater along a rearward portion of the helical spiral than along the forward portion of the helical spiral (relative to advancement of the closure member 30 when being inserted into receiving member 20). By having the peak thickness (or peak complementary opening) of the inner thread of receiving part 20 maintained substantially consistent (and approximately equal to the greatest peak thickness $T_{PK}$ of the closure member's thread), larger clearance of the forward portion of the closure member's thread (having a smaller peak thickness $T_{PK}$) is permitted within the receiving member's thread than is permitted for the rearward portion of the closure member's thread (having the greatest peak thickness $T_{PK}$) when the closure member 30 is being inserted into the receiving member 20.

Figure 6:
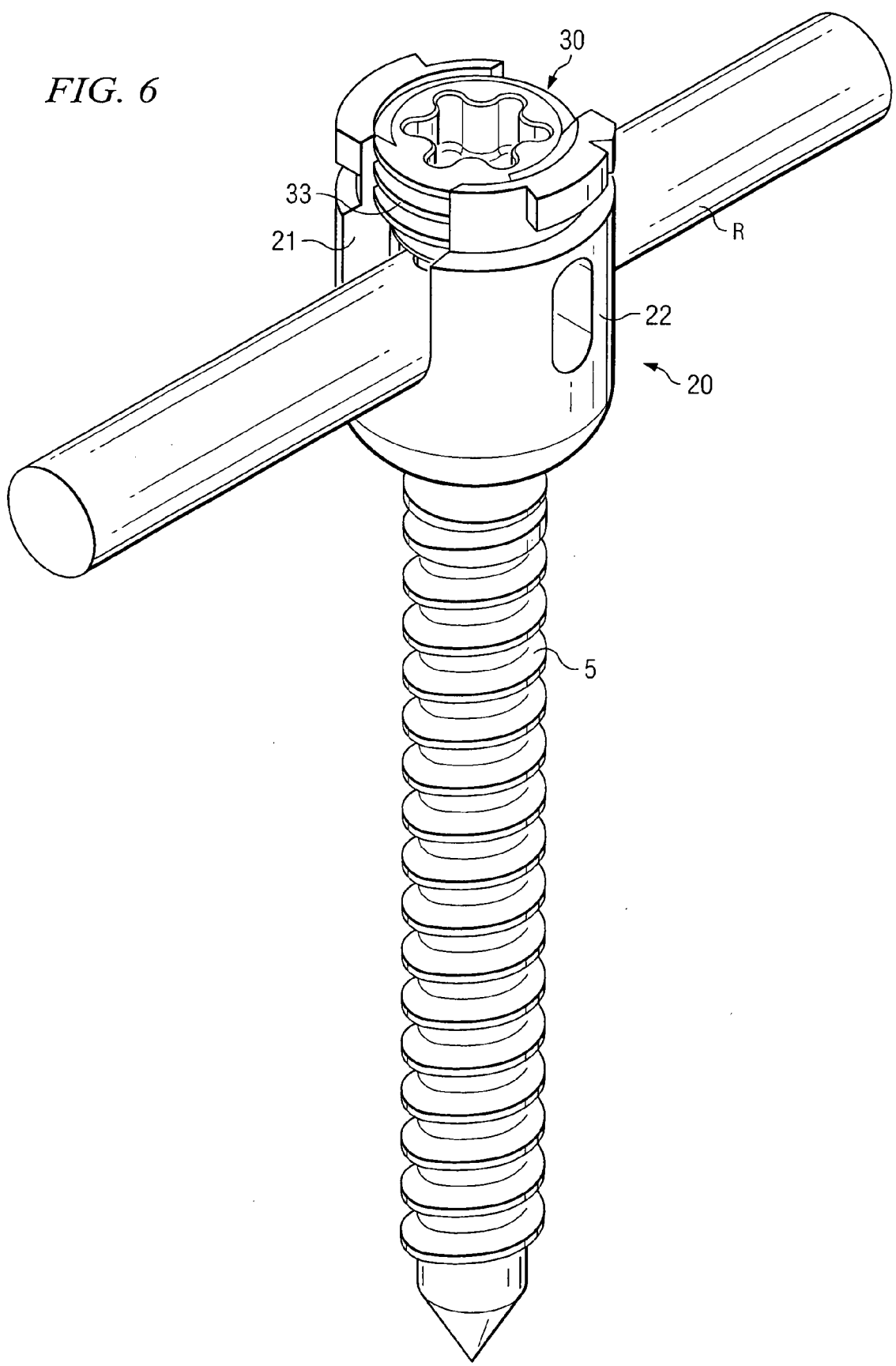
FIG. 6 shows an isometric view of the example medical implant device 10 of FIGS. 1–5.

FIG. 6 shows an isometric view of the example medical implant device 10 of FIGS. 1–5. As shown, medical implant device 10 includes pedicle screw 5, receiving part 20 having noncontiguous walls 21 and 22, rod R inserted within a channel of receiving part 20, and closure member 30. As described above, closure member 30 engages walls 21 and 22 and applies pressure thereto causing receiving part 20 to effectively clamp about rod R, thereby positionally securing rod R relative to pedicle screw 5.

Figure 7:
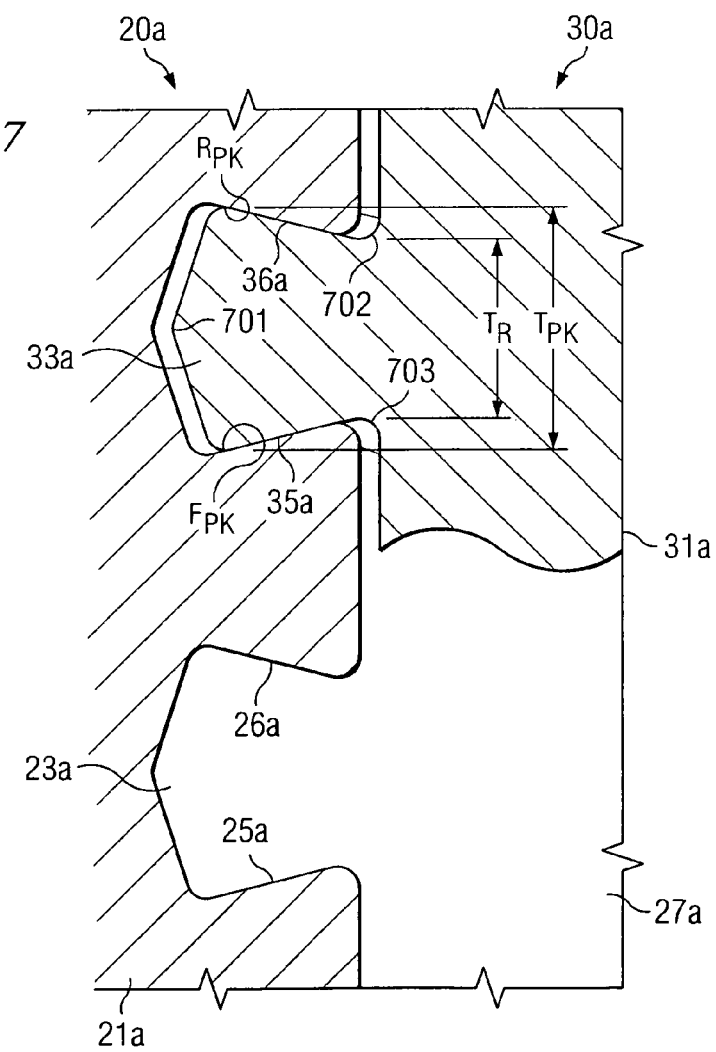
FIG. 7 shows a cross-section view of another example thread that may be employed for a closure member interlocking with complementary (or female) thread that may be employed for a receiving member in accordance with one embodiment.

FIG. 7 shows an alternative embodiment of an interlocking configuration of the closure member (labeled 30a in this embodiment) and noncontiguous receiving member (labeled 20a in this embodiment) of a medical implant device, which aids in preventing splaying of the noncontiguous receiving member. More particularly, FIG. 7 shows a cross-section of a portion of a closure member 30a and receiving member 20a of one side of a center longitudinal axis 31a of the channel of receiving member 20a and of closure member 30a (i.e., axis 31a in this example corresponds to axis 28 of FIG. 2 and axis 31 of FIG. 3). It should be recognized that as with the example embodiment described above with FIGS. 1–6, the opposite side of the center longitudinal axis 31a (not shown in FIG. 7) substantially mirrors the side shown in FIG. 7. As with receiving member 20 described above in connection with FIG. 2, receiving member 20a includes a longitudinal channel formed by a plurality of noncontiguous walls that include an inner (female) thread that forms a helical spiral about a center longitudinal axis of the channel (axis 31a). One of such plurality of noncontiguous walls, labeled 21a, is shown in FIG. 7. Wall 21a is arranged in receiving member 20a just as wall 21 is arranged in receiving member 20 described above in connection with FIG. 2. Additionally, as with receiving member 20 described above in connection with FIG. 2, receiving member 20a would further include a wall arranged as wall 22 of FIG. 2 that likewise include an inner (female) thread that is configured as a helical spiral about a center longitudinal axis of the channel (axis 31*a*) and that is configured as the inner thread described further below for wall 21*a*.

Closure member (e.g., a set screw) 30*a* is adapted to interlock with receiving member 20*a*. That is, closure member 30*a* includes an outer (male) thread 33*a* configured to interlock with the inner (female) thread of the noncontiguous walls of receiving member 20*a* in order to close such receiving member 20*a*. Thus, as with receiving member 20 described above, receiving member 20*a* has a central, longitudinal bore in which closure member 30*a* is received. Receiving member 20*a* also includes interlocking features (e.g., "inner" or "female" thread) cut into its noncontiguous side walls, such as the inner thread 23*a* that can be seen in the lower portion of FIG. 7 having closure member 30*a* shown in phantom. Inner thread 23*a* has a rearward-facing surface 25*a* (which faces the opening of bore 27*a*, i.e., faces the direction opposite the direction of advancement of closure member 30*a* when it is being inserted into receiving member 20*a*) and forward-facing surface 26*a* (which faces the direction of advancement of closure member 30*a* when it is being inserted into receiving member 20*a*). Surfaces 25*a* and 26*a* are cut in such a manner to form a complementary interlocking geometry relative to the geometry of interlocking feature 33*a* (e.g., "outer" or "male" thread) of the closure member 30*a*.

In this example, closure member (e.g., set screw) 30*a* includes external interlocking features (e.g., "outer" or "male" thread) 33*a* centered about axis 31*a* in the form of a helical pattern (half of which is shown in FIG. 7). In this example, interlocking features 33*a* include leading-edge surface 35*a* and trailing-edge surface 36*a* configured to form a pattern suitable for mating to surfaces 25*a* and 26*a* of interlocking feature 23*a* of receiving member 20*a* as described further herein. In this example, the trailing-edge surface 36*a* has a rearward peak $R_{PK}$ (i.e., the point on the trailing-edge surface that is most rearward relative to the direction of advancement of closure member 30*a* when being inserted into receiving member 20*a*) that is between the root 702 and crest 701 of trailing-edge surface 36*a*. Further, the leading-edge surface 35*a* has a forward peak $F_{PK}$ (i.e., the point on the leading-edge surface that is most forward relative to the direction of advancement of closure member 30*a* when being inserted into receiving member 20*a*) that is between the root 703 and crest 701 of leading-edge surface 35*a*. Thus, the thickness $T_R$ at the root of outer thread 33*a* is smaller than the thickness $T_{PK}$ at a point crestward along thread 33*a*. That is, the peak thickness $T_{PK}$ of thread 33*a* occurs at a point between its root and crest. In this example, the crest 701 of thread 33*a* is configured to be forward of the root 702 of trailing edge 36*a* and rearward of the root 703 of leading edge 35*a*.

Thus, when closure member 30*a* is joined together with receiving member 20*a*, forward-facing surface 26*a* of receiving member 20*a* engages with trailing-edge surface 36*a* of thread 33*a* of closure member 30*a*, while rearward-facing surface 25*a* of receiving member 20*a* engages with leading-edge surface 35*a* of thread 33*a* of closure member 30*a*. Because the peak thickness $T_{PK}$ of the female thread 23*a* of receiving member 20*a* is greater than its root thickness $T_R$, a mechanical interlock is created between the female (or inner) thread 23*a* of receiving member 20*a* and the male (or outer) thread 33*a* of closure member 30*a* such that surfaces 25*a* and 26*a* of female thread 23*a* cannot be separated from surfaces 35*a* and 36*a* of thread 33*a*. In this way, closure member 30*a* forbids the noncontiguous walls (e.g., wall 21*a* and other wall(s) not shown, such as wall 22 in the example of FIG. 2) from separating or splaying relative to such closure member 30*a*. As with the example embodiment of FIGS. 1–6, when implemented in a medical implant device 10, this action prevents the elongated member R from obtaining room to rock within transverse channel 29 which is beneficial because, as mentioned above, if elongated member R obtained room to rock it could cause device failure and required replacement and/or injury to the patient.

Figure 8:
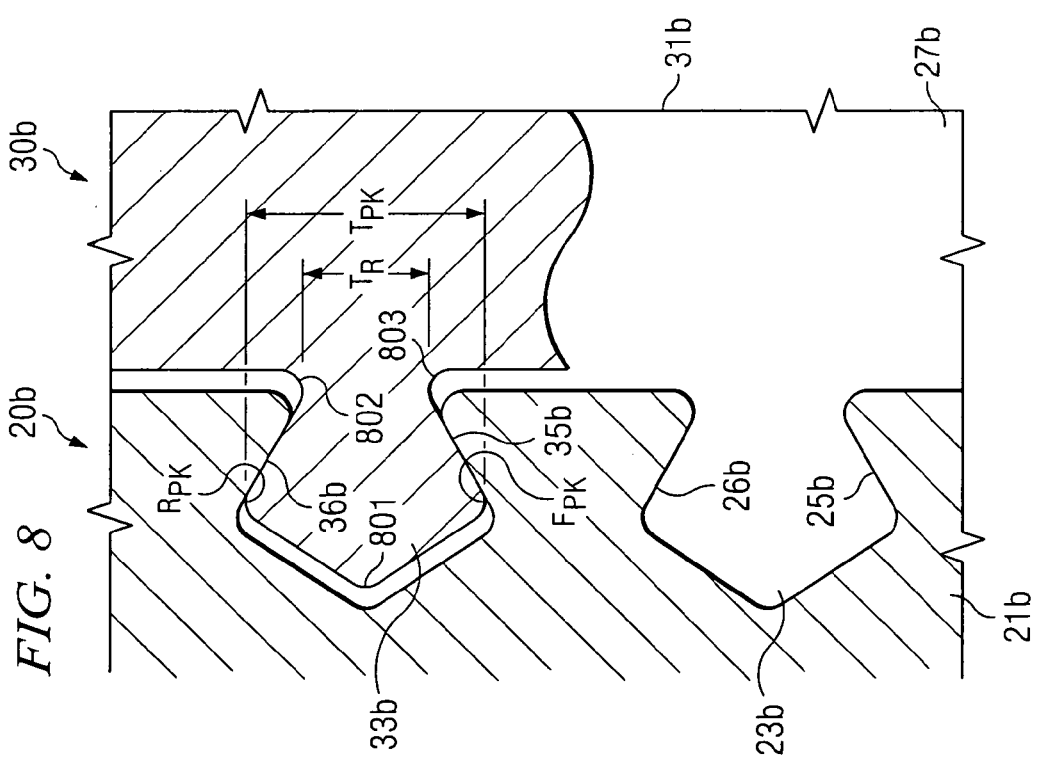
FIG. 8 shows a cross-section view of another example thread that may be employed for a closure member interlocking with complementary (or female) thread that may be employed for a receiving member in accordance with one embodiment.

FIG. 8 shows another alternative embodiment of an interlocking configuration of the closure member (labeled 30*b* in this embodiment) and noncontiguous receiving member (labeled 20*b* in this embodiment) of a medical implant device, which aids in preventing splaying of the noncontiguous receiving member. More particularly, FIG. 8 shows a cross-section of a portion of a closure member 30*b* and receiving member 20*b* of one side of a center longitudinal axis 31*b* of the channel of receiving member 20*b* and of closure member 30*b* (i.e., axis 31*b* in this example corresponds to axis 28 of FIG. 2 and axis 31 of FIG. 3). It should be recognized that as with the example embodiment described above with FIGS. 1–6, the opposite side of the center longitudinal axis 31*b* (not shown in FIG. 8) substantially mirrors the side shown in FIG. 8. As with receiving member 20 described above in connection with FIG. 2, receiving member 20*b* includes a longitudinal channel formed by a plurality of noncontiguous walls that include an inner (female) thread configured as a helical spiral about a center longitudinal axis of the channel (axis 31*b*). One of such plurality of noncontiguous walls, labeled 21*b*, is shown in FIG. 8. Wall 21*b* is arranged in receiving member 20*b* just as wall 21 is arranged in receiving member 20 described above in connection with FIG. 2. Additionally, as with receiving member 20 described above in connection with FIG. 2, receiving member 20*b* would further include a wall arranged as wall 22 of FIG. 2 that likewise include an inner (female) thread that forms a helical spiral about a center longitudinal axis of the channel (axis 31*b*) and that is configured as the inner thread described further below for wall 21*b*.

Closure member (e.g., a set screw) 30*b* is adapted to interlock with receiving member 20*b*. That is, closure member 30*b* includes an outer (male) thread 33*b* configured to interlock with the inner (female) thread of the noncontiguous walls of receiving member 20*b* in order to close such receiving member 20*b*. Thus, as with receiving member 20 described above, receiving member 20*b* has a central, longitudinal bore in which closure member 30*b* is received. Receiving member 20*b* also includes interlocking features (e.g., "inner" or "female" thread) cut into its noncontiguous side walls, such as the inner thread 23*b* that can be seen in the lower portion of FIG. 8 having closure member 30*b* shown in phantom. Inner thread 23*b* has a rearward-facing surface 25*b* (which faces the opening of bore 27*b*, i.e., faces the direction opposite the direction of advancement of closure member 30*b* when it is being inserted into receiving member 20*b*) and forward-facing surface 26*b* (which faces the direction of advancement of closure member 30*b* when it is being inserted into receiving member 20*b*). Surfaces 25*b* and 26*b* are cut in such a manner to form a complementary interlocking geometry relative to the geometry of interlocking feature 33*b* (e.g., "outer" or "male" thread) of the closure member 30*b*.

In this example, closure member (e.g., set screw) 30*b* includes external interlocking features (e.g., "outer" or "male" thread) 33*b* centered about axis 31*b* in the form of a helical pattern (half of which is shown in FIG. 8). In this example, interlocking features 33b include leading-edge surface 35b and trailing-edge surface 36b configured to form a pattern suitable for mating to surfaces 25b and 26b of interlocking feature 23b of receiving member 20b as described further herein. In this example, the trailing-edge surface 36b has a rearward peak $R_{PK}$ (i.e., the point on the trailing-edge surface that is most rearward relative to the direction of advancement of closure member 30b when being inserted into receiving member 20b) that is between the root 802 and crest 801 of trailing-edge surface 36b. Further, the leading-edge surface 35b has a forward peak $F_{PK}$ (i.e., the point on the leading-edge surface that is most forward relative to the direction of advancement of closure member 30b when being inserted into receiving member 20b) that is between the root 803 and crest 801 of leading-edge surface 35b. Thus, the thickness $T_R$ at the root of outer thread 33b is smaller than the thickness $T_{PK}$ at a point crestward along thread 33b. That is, the peak thickness $T_{PK}$ of thread 33b occurs at a point between its root and crest. In this example, the crest 801 of thread 33b is configured to be forward of the root 802 of trailing edge 36b and rearward of the root 803 of leading edge 35b. Thus, when closure member 30b is joined together with receiving member 20b, forward-facing surface 26b of receiving member 20b engages with trailing-edge surface 36b of thread 33b of closure member 30b, while rearward-facing surface 25b of receiving member 20b engages with leading-edge surface 35b of thread 33b of closure member 30b. Because the peak thickness $T_{PK}$ of the female thread 23b of receiving member 20b is greater than its root thickness $T_R$, a mechanical interlock is created between the female (or inner) thread 23b of receiving member 20b and the male (or outer) thread 33b of closure member 30b such that surfaces 25b and 26b of female thread 23b cannot be separated from surfaces 35b and 36b of thread 33b. In this way, closure member 30b forbids the noncontiguous walls (e.g., wall 21b and other wall(s) not shown, such as wall 22 in the example of FIG. 2) from separating or splaying relative to such closure member 30b. As with the example embodiment of FIGS. 1–6, when implemented in a medical implant device 10, this action prevents the elongated member R from obtaining room to rock within transverse channel 29 which is beneficial because, as mentioned above, if elongated member R obtained room to rock it could cause device failure and required replacement and/or injury to the patient.

Figure 9:
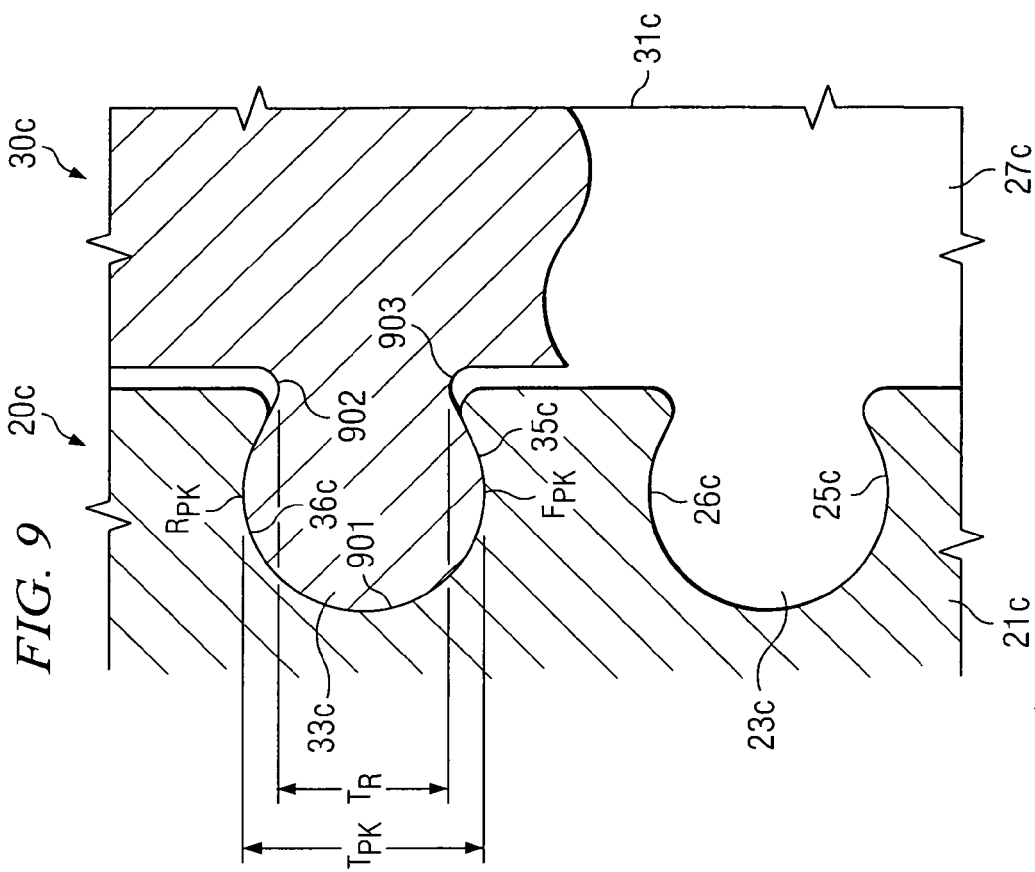
FIG. 9 shows a cross-section view of still another example thread that may be employed for a closure member interlocking with complementary (or female) thread that may be employed for a receiving member in accordance with one embodiment.

FIG. 9 shows still another alternative embodiment of an interlocking configuration of the closure member (labeled 30c in this embodiment) and noncontiguous receiving member (labeled 20c in this embodiment) of a medical implant device, which aids in preventing splaying of the noncontiguous receiving member. More particularly, FIG. 9 shows a cross-section of a portion of a closure member 30c and receiving member 20c of one side of a center longitudinal axis 31c of the channel of receiving member 20c and of closure member 30c (i.e., axis 31c in this example corresponds to axis 28 of FIG. 2 and axis 31 of FIG. 3). It should be recognized that as with the example embodiment described above with FIGS. 1–6, the opposite side of the center longitudinal axis 31c (not shown in FIG. 9) substantially mirrors the side shown in FIG. 9. As with receiving member 20 described above in connection with FIG. 2, receiving member 20c includes a longitudinal channel formed by a plurality of noncontiguous walls that include an inner (female) thread that is configured as a helical spiral about a center longitudinal axis of the channel (axis 31c). One of such plurality of noncontiguous walls, labeled 21c, is shown in FIG. 9. Wall 21c is arranged in receiving member 20c just as wall 21 is arranged in receiving member 20 described above in connection with FIG. 2. Additionally, as with receiving member 20 described above in connection with FIG. 2, receiving member 20c would further include a wall arranged as wall 22 of FIG. 2 that likewise include an inner (female) thread that forms a helical spiral about a center longitudinal axis of the channel (axis 31c) and that is configured as the inner thread described further below for wall 21c.

Closure member (e.g., a set screw) 30c is adapted to interlock with receiving member 20c. That is, closure member 30c includes an outer (male) thread 33c configured to interlock with the inner (female) thread of the noncontiguous walls of receiving member 20c in order to close such receiving member 20c. Thus, as with receiving member 20 described above, receiving member 20c has a central, longitudinal bore in which closure member 30c is received. Receiving member 20c also includes interlocking features (e.g., "inner" or "female" thread) cut into its noncontiguous side walls, such as the inner thread 23c that can be seen in the lower portion of FIG. 9 having closure member 30c shown in phantom. Inner thread 23c has a rearward-facing surface 25c (which faces the opening of bore 27c, i.e., faces the direction opposite the direction of advancement of closure member 30c when it is being inserted into receiving member 20c) and forward-facing surface 26c (which faces the direction of advancement of closure member 30c when it is being inserted into receiving member 20c). Surfaces 25c and 26c are cut in such a manner to form a complementary interlocking geometry relative to the geometry of interlocking feature 33c (e.g., "outer" or "male" thread) of the closure member 30c.

In this example, closure member (e.g., set screw) 30c includes external interlocking features (e.g., "outer" or "male" thread) 33c centered about axis 31c in the form of a helical pattern (half of which is shown in FIG. 9). In this example, interlocking features 33c include leading-edge surface 35c and trailing-edge surface 36c configured to form a pattern suitable for mating to surfaces 25c and 26c of interlocking feature 23c of receiving member 20c as described further herein. In this example, the trailing-edge surface 36c has a rearward peak $R_{PK}$ (i.e., the point on the trailing-edge surface that is most rearward relative to the direction of advancement of closure member 30c when being inserted into receiving member 20c) that is between the root 902 and crest 901 of trailing-edge surface 36c. Further, the leading-edge surface 35c has a forward peak $F_{PK}$ (i.e., the point on the leading-edge surface that is most forward relative to the direction of advancement of closure member 30c when being inserted into receiving member 20c) that is between the root 903 and crest 901 of leading-edge surface 35c. Thus, the thickness $T_R$ at the root of outer thread 33c is smaller than the thickness $T_{PK}$ at a point crestward along thread 33c. That is, the peak thickness $T_{PK}$ of thread 33c occurs at a point between its root and crest. In this example, the crest 901 of thread 33c is configured to be forward of the root 902 of trailing edge 36c and rearward of the root 903 of leading edge 35c. As shown, the trailing edge 36c is a curvature that progresses rearwardly from root 902 to rearward peak $R_{PK}$ and then progresses forwardly from rearward peak $R_{PK}$ to crest 901. Similarly, the leading edge 35c is a curvature that progresses forwardly from root 903 to forward peak $F_{PK}$ and then progresses rearwardly from forward peak $F_{PK}$ to crest 901.

Thus, when closure member 30c is joined together with receiving member 20c, forward-facing surface 26c of receiving member 20c engages with trailing-edge surface 36c of thread 33c of closure member 30c, while rearward-facing surface 25c of receiving member 20c engages with leading-edge surface 35c of thread 33c of closure member 30c. Because the peak thickness $T_{PK}$ of the female thread 23c of receiving member 20c is greater than its root thickness $T_R$, a mechanical interlock is created between the female (or inner) thread 23c of receiving member 20c and the male (or outer) thread 33c of closure member 30c such that surfaces 25c and 26c of female thread 23c cannot be separated from surfaces 35c and 36c of thread 33c. In this way, closure member 30c forbids the noncontiguous walls (e.g., wall 21c and other wall(s) not shown, such as wall 22 in the example of FIG. 2) from separating or splaying relative to such closure member 30c. As with the example embodiment of FIGS. 1–6, when implemented in a medical implant device 10, this action prevents the elongated member R from obtaining room to rock within transverse channel 29 which is beneficial because, as mentioned above, if elongated member R obtained room to rock it could cause device failure and required replacement and/or injury to the patient.

Figure 10:
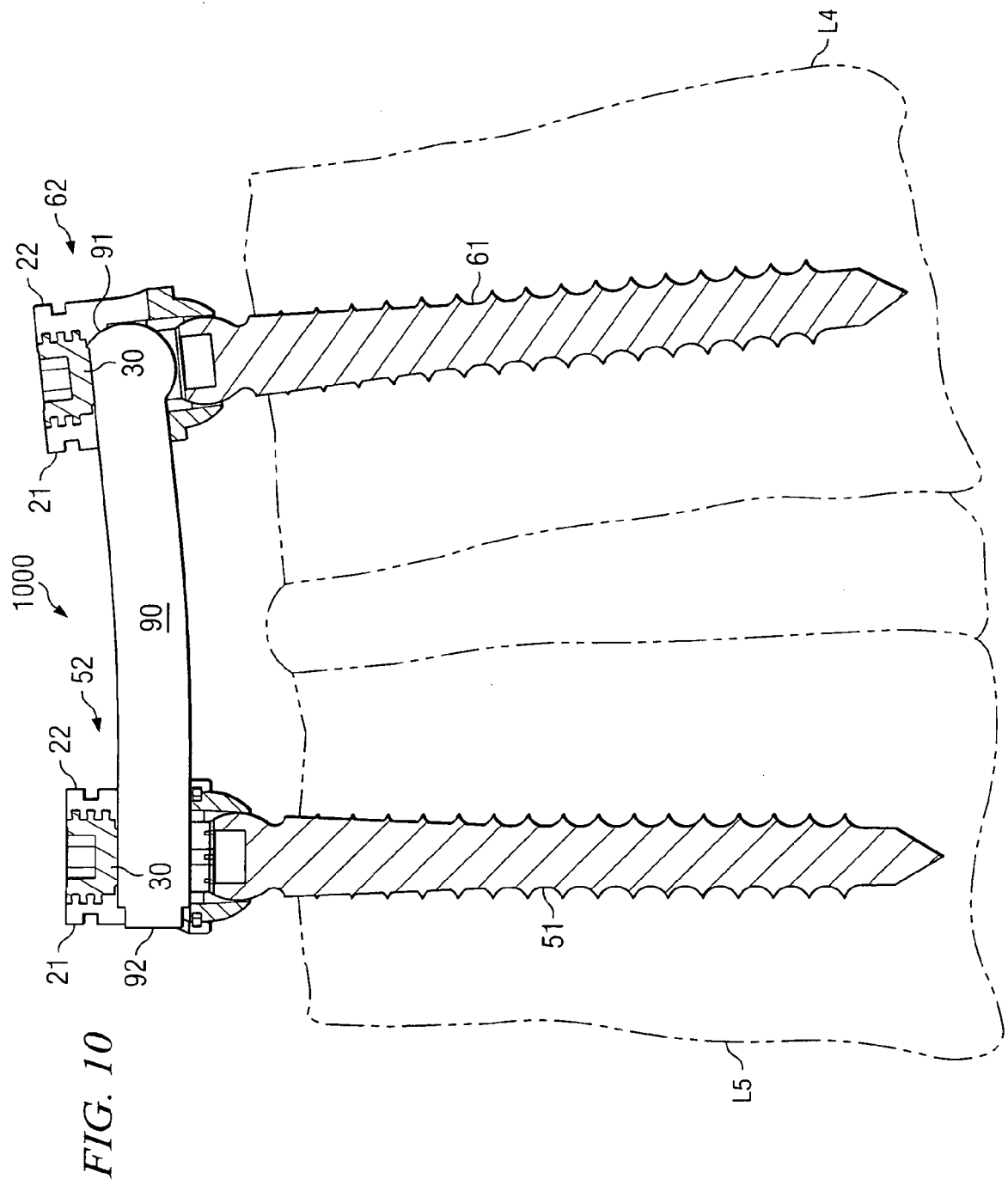
FIG. 10 shows an example medical implant device that utilizes a receiving member and closure member in accordance with one embodiment of the present invention.

FIG. 10 shows an example medical implant device 1000. The example medical implant device 1000 of FIG. 10 is described further in co-pending and commonly assigned U.S. patent application Ser. No. 10/690,211 filed Oct. 21, 2003 titled "SYSTEM AND METHOD FOR STABILIZATION OF INTERNAL STRUCTURES" (hereafter "the '211 patent application), the disclosure of which is hereby incorporated herein by reference. More specifically, medical implant device 1000 is a stabilization device that includes pedicle screws (or "anchors") 61 and 51 that are inserted into vertebrae of a patient's spine, such as vertebrae L4 and L5, respectively, in this example. Assemblies 52 and 62 are coupled to pedicle screws 51 and 61, respectively. Such assemblies 52 and 62 each form a receiving member for receiving closure member (e.g., set screw) 30. Generally, such receiving member formed by assemblies 52 and 62 is a noncontiguous (e.g., open-back member) having at least two walls, such as walls 21 and 22, that are separated by slots. As described further herein, closure member 30 and walls 21 and 22 are formed to have complementary threads that are formed in a manner that aids in preventing splaying of the receiving members, such as with the example configurations described above in FIGS. 1–9. In the specific implementation shown, closure member 30 and walls 21 and 22 of the receiving member are dovetail configurations, such as described above with FIGS. 1–6. Of course, other interlocking configurations, such as those of FIGS. 7–9, may be used in alternative implementations. As further shown in FIG. 10, a brace (or "rod") 90 extends from assembly 52 to assembly 62, and closure members (e.g., set screws) 30 are used for securing a first end 92 of brace 90 to pedicle screw 51 and the other end 91 of brace 90 to pedicle screw 61.

In implanting such stabilization device 1000, in accordance with one embodiment, a surgeon identifies the desired vertebral levels and pedicle positions via standard techniques. Once the target vertebrae (vertebra levels L4 and L5 in this example) are identified, a small incision is made through the patient's skin and a tracking needle (or other device) is inserted to pinpoint exactly where each anchor is to be placed. A fluoroscope, or other x-ray technique, is used to properly position the tracking needle. Once the proper position is located, a first guide wire (K wire) is positioned with its distal end against the pedicle of vertebrae L4, and a second guide wire (K wire) is positioned with its distal end against the pedicle of vertebrae L5. The surgeon then slides a series of continuing larger sized dilators down each of these guide wires.

Approximately four or five dilators are used until a diameter suitable for passing the pedicle screw and its extensions is achieved. A tap is sent down over the K wire to tap a hole into the pedicle in preparation for receiving the anchor, which in this case is a pedicle screw. This tap will usually be a size slightly smaller than the pedicle screw thread size selected for that patient and that level.

After the hole is tapped and the K wire and the inner dilators are removed, the surgeon is ready to introduce the anchor (e.g., pedicle screw) into the vertebrae. Prior to inserting the anchor, brace 90 is attached to screw 51 to form a brace-screw assembly. This assembly is then positioned at the distal end of a first cannula and a screwdriver or wrench is inserted into the first cannula and attached to the proximal end of brace 90. The entire assembly is then inserted into a remaining dilator. The screwdriver engages with proximal end 91 of brace 90 so as to allow the surgeon to screw pedicle screw 51 into the pre-tapped hole in vertebrae L5. Pressure on the screwdriver forces the screw to be in-line with the brace, which, in turn, is in-line with the screwdriver.

This same procedure may be repeated for each additional level, in this case level L4, except that screw 61 has assembly 62 affixed thereto. Assembly 62 is adapted to receive the proximal end 91 of brace 90 as is more fully described below.

Once both screws 51 and 61 are in place in vertebrae L5 and L4, respectively, the remaining dilators are removed and, the surgeon slides a blunt dissection tool into the skin incision and gently parts the muscle bundle below the skin between vertebrae L4 and L5. Alternatively, the blunt dissection tool could go down the second cannula (through which screw 61 was inserted) and, starting at the bottom of the second cannula, work open the muscle bundle between the cannula working upward as far as is necessary. Using this procedure, the muscles (and other tissue), only need be separated to a point where the brace 90 must pass. Thus, the separation need not go to the skin level. This reduces patient trauma even further.

Once an opening in the muscles has been developed between the first and second cannulas, brace 90 is then positioned, by pivoting (as shown in FIG. 2D of the '211 patent application), by sliding a tool down the first cannula in which it resides to engage the proximal end 91 of brace 90.

As shown in FIG. 10, after all angular and lateral adjustments are made, set screws 30 are introduced down the first and second cannulas to lock each end of brace 90 to its respective pedicle screw. Once the proximal end 91 of brace 90 is snapped in place to screw 61 and set screws 30 are tightened, the first and second cannulas can be removed and the incision closed. The process of using such a stabilization device 900 in which a brace-screw assembly (of brace 90 attached to pedicle screw 51) are first inserted via a first cannula and attached to a vertebrae (e.g., vertebrae L5) and then brace 90 is pivoted such that its first end 92 remains positioned over pedicle screw 51 and its opposite end 91 is positioned over pedicle screw 61 is described further in the '211 patent application.

It should be understood that application of the various embodiments of an interlocking closure member and receiving member are not limited to the example medical implant device 1000 of FIG. 10. Rather, such embodiments may be equally utilized within various other types of medical implant devices for closing noncontiguous walls of a receiving member included in such medical implant devices, and any such application is intended to be within the scope of the present invention.

In view of the above, various embodiments of a closure member and a complementary, noncontiguous receiving member of a medical implant device are provided in which the closure member and receiving member are configured to interlock in a manner that aids in preventing splaying of the receiving member. More particularly, various embodiments are provided in which at least one point on the trailing-edge surface of a thread of the closure member is rearward of the root of such trailing-edge surface relative to the advancement of the closure member when being inserted into the receiving member, and at least one point on the leading-edge surface of a thread of the closure member is forward of the root of such leading-edge surface relative to the advancement of the closure member when being inserted into the receiving member. Thus, a rearward peak is provided on the trailing-edge surface at some point crestward of its root, and a forward peak is provided on the leading-edge surface at some point crestward of its root. For instance, in the example dovetail configuration of FIGS. 1–6, the rearward peak of the thread is provided substantially at the crest of the trailing edge and the forward peak of the thread is provided substantially at the crest of the leading edge. In other example embodiments, such as those of FIGS. 7–9 above, the rearward peak of the thread is provided on the trailing edge between the root and crest, and the forward peak of the thread is provided on the leading edge between the root and crest. In certain embodiments, such as those of FIGS. 7–9, the trailing edge of the thread has a point between the crest and root that is rearward of the root, and the crest is at least horizontal with, and in some implementations forward of, the trailing edge's root. Additionally, the leading edge of the thread has a point between the crest and root that is forward of the root, and the crest is at least horizontal with, and in some implementations rearward of, the leading edge's root.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A medical implant device comprising:
a receiver member including a plurality of wall sections defining a longitudinal bore, wherein said wall sections have an inner threaded portion; and
a closure member including a rearward end, a forward end, a substantially cylindrical body having a longitudinal axis and an outer threaded portion for threaded engagement with said inner threaded portion of said receiver member, wherein the outer thread portion includes a screw form for a given cross-section of thread through a plane which includes the longitudinal axis, the screw form comprising:
a rearward-facing thread surface having a substantially straight sloped portion and at least two non-contiguous curve portions, such that a point on the rearward-facing thread surface at a root of the thread surface is farther from the forward end than a point on the rearward-facing thread surface at a crest of the thread surface when measured along a line parallel to the longitudinal axis; wherein a maximum thickness of the thread occurs at a point closer to the crest of the thread than the root of the thread.

2. The medical implant device of claim 1 wherein said receiver member also includes a transverse channel substantially perpendicular to said bore.

3. The medical implant device of claim 1 wherein said receiver member is a part of a bone fixation device.

4. The medical implant device of claim 3 wherein said bone fixation device is a bone screw.

5. The medical implant device of claim 3 wherein said bone fixation device is a spinal hook.

6. The medical implant device of claim 1 wherein said closure member is a set screw.

7. The medical implant device of claim 1 wherein the screw form further comprises: a forward-facing thread surface having a substantially straight sloped portion and at least two non-contiguous curve portions, such that a point on the forward-facing thread surface at a root of the forward facing thread surface is closer to the forward end than a point on the forward-facing thread surface at a crest of the forward facing thread surface when measured along a line parallel to the longitudinal axis.

8. The medical implant device of claim 1 wherein an angle measured between the substantially straight sloped portion of the forward-facing thread surface and a the substantially straight sloped portion of the rearward facing thread surface is between about 2 degrees and 40 degrees.

9. The medical implant device of claim 8 wherein said included angle is about 15 degrees.

10. The medical implant device of claim 1 wherein said outer threaded portion is configured as a helical spiral about said body, and wherein the thickness of said outer threaded portion at its crest varies along the helical spiral.

11. The medical implant device of claim 1 wherein said outer threaded portion is configured as a helical spiral about said body, and wherein the thickness of said outer threaded portion at its root varies along the helical spiral.

12. The medical implant device of claim 1 wherein said outer threaded portion is configured as a helical spiral about said body, and wherein a peak thickness of said outer threaded portion occurs crestward of said outer threaded portion's root, and wherein the thickness of said peak thickness varies along said helical spiral.

13. The medical implant device of claim 12 wherein said thickness of said peak thickness is thicker at a rearward portion of said helical spiral than at a forward portion of said helical spiral relative to the direction of advancement of said closure member when being inserted into said receiving member.

14. A medical implant device comprising:
a receiver member including a plurality of noncontiguous wall sections defining a longitudinal bore, wherein said plurality of noncontiguous wall sections include a female threaded portion configured as a helical spiral about a center longitudinal axis of the bore; and
a closure member including a substantially cylindrical body having a forward end, a rearward end, a longitudinal axis and a male threaded portion for interlocking engagement with said female threaded portion of said receiver member, wherein the male threaded portion includes a screw form for a given cross-section of thread through a plane parallel to the longitudinal axis, the screw form comprising: a rearward-facing thread surface having a substantially straight sloped portion and at least two non-contiguous curve portions, such that a point on the rearward-facing thread surface at a root of the thread is farther from the forward end than a point on the rearward-facing thread surface at a crest of the thread when measured along a line that is parallel to the longitudinal axis: wherein a maximum thickness of the thread occurs at a point closer to the crest of the thread than the root of the thread.

15. The medical implant device of claim 14 wherein said receiver member also includes a transverse channel substantially perpendicular to said bore.

16. The medical implant device of claim 14 wherein said receiver member is a part of a bone fixation device.

17. The medical implant device of claim 16 wherein said bone fixation device is one selected from the group consisting of: a bone screw and a spinal hook.

18. The medical implant device of claim 14 wherein said closure member is a set screw.

19. The medical implant device of claim 14 wherein said male threaded portion is configured as a helical spiral about said body, and wherein thickness at said at least one point crestward of its root varies along the helical spiral.

20. The medical implant device of 14 wherein said male threaded portion is configured as a helical spiral about said body, and wherein the thickness of said male threaded portion at its root and the thickness of said male threaded portion at its crest vary along the helical spiral.

21. The medical implant device of claim 14 wherein the screw form further comprises: a forward-facing thread surface having a substantially straight sloped portion and at least two non-contiguous curve portions, such that a point on the forward-facing thread surface at a root of the forward facing thread surface is closer to the forward end than a point on the forward-facing thread surface at a crest of the forward facing thread surface when measured along a line parallel to the longitudinal axis.

22. A noncontiguous receiver member and complementary closure member included in a medical implant device, comprising:
said noncontiguous receiver member having a plurality of noncontiguous wall sections separated by a slot, said wall sections at least partially defining a longitudinal bore, wherein said plurality of noncontiguous wall sections include a female threaded portion that forms substantially a helical spiral about a center longitudinal axis of the bore; and
said complementary closure member having a substantially cylindrical body portion and male threaded portion that forms substantially a helical spiral about a center longitudinal axis of the body portion, wherein the male threaded portion includes a screw form for a given cross-section of thread through the longitudinal axis, the screw form comprising: a rearward-facing thread surface having a substantially straight sloped portion and at least two non-contiguous curve portions, such that a point on the rearward-facing thread surface at a root of the thread is farther from a forward end of the closure member than a point on the rearward-facing thread surface at a crest of the thread to form a rearward peak of said male threaded portion on its trailing-edge surface at some point crestward of its root, and wherein a forward peak of said male threaded portion is provided on its leading-edge surface at some point crestward of its root; wherein the distance between the rearward peak and the forward peak provides a maximum thickness of the thread: wherein the maximum thickness of the thread occurs at a point closer to the crest of the thread than the root of the thread.

23. The noncontiguous receiver member and complementary closure member of claim 22 wherein said rearward peak occurs at the crest of said trailing-edge surface.

24. The noncontiguous receiver member and complementary closure member of claim 23 wherein said forward peak occurs at the crest of said leading-edge surface.

25. The noncontiguous receiver member and complementary closure member of claim 22 wherein said receiver member also includes a transverse channel substantially perpendicular to said longitudinal bore.

26. The noncontiguous receiver member and complementary closure member of claim 22 wherein said receiver member is a part of a bone fixation device.

27. The noncontiguous receiver member and complementary closure member of claim 26 wherein said bone fixation device is one selected from the group consisting of: a bone screw and a spinal hook.

28. The medical implant device of claim 22 wherein the screw form further comprises: a forward-facing thread surface having a substantially straight sloped portion and at least two non-contiguous curve portions, such that a point on the forward-facing thread surface at a root of the forward facing thread surface is closer to the forward end than a point on the forward-facing thread surface at a crest of the forward facing thread surface when measured along a line parallel to the longitudinal axis.

29. A medical implant device comprising:
a means for receiving a closure means, the receiving means including a plurality of noncontiguous wall sections at least partially defining a longitudinal bore, wherein said wall sections have an inner threaded portion; and
said closure means for engaging said plurality of noncontiguous wall sections, the closure means including a substantially cylindrical body having an outer threaded portion for threaded engagement with said inner threaded portion of said receiving means,
wherein said outer threaded portion includes a screw form for a given cross-section of thread through a longitudinal axis of the closure means, the screw form comprising: a rearward-facing thread surface having a substantially straight sloped portion and at least two non-contiguous curve portions, such that a point on the rearward-facing thread surface at a root of the thread is farther from a forward end of the closure means than a point on the rearward-facing thread surface at a crest of the thread when measured along a line parallel to the longitudinal axis: wherein a maximum thickness of the thread occurs at a point closer to the crest of the thread than the root of the thread.

30. The medical implant device of claim 29 wherein the screw form further comprises: a forward-facing thread surface having a substantially straight sloped portion and at least two non-contiguous curve portions, such that a point on the forward-facing thread surface at a root of the forward facing thread surface is closer to the forward end than a point on the forward-facing thread surface at a crest of the forward facing thread surface when measured along a line parallel to the longitudinal axis.

31. A medical implant device comprising:

a receiver member including a plurality of noncontiguous wall sections at least partially defining a longitudinal bore, wherein said plurality of noncontiguous wall sections include a female threaded portion arranged as a helical spiral about a center longitudinal axis of the bore; and a closure member including a substantially cylindrical body having a male threaded portion for interlocking engagement with said female threaded portion of said receiver member, wherein said male threaded portion includes a trailing edge having a root adjacent said body and having a crest at a point on said trailing edge that is furthest from a longitudinal axis centered in said cylindrical body when measured along a line perpendicular to said longitudinal axis, wherein said outer threaded portion includes a screw form for a given cross-section of thread through a plane which includes the longitudinal axis, the screw form comprising:

a rearward-facing thread surface having a substantially straight sloped portion and at least two non-contiguous curve portions, such that a point on the rearward-facing thread surface at a root of the thread is farther from a forward end of the closure member than a point on the rearward-facing thread surface at a crest of the thread, and a forward-facing thread surface having a substantially straight sloped portion and at least two non-contiguous curve portions, such that a point on the forward-facing thread surface at a root of the forward facing thread surface is closer to the forward end than a point on the forward-facing thread surface at a crest of the forward facing thread surface when measured along a line parallel to the longitudinal axis: wherein a maximum thickness of the thread occurs at a point closer to the crest of the thread than the root of the thread.

* * * * *